United States Patent
Welker et al.

(10) Patent No.: US 8,210,058 B2
(45) Date of Patent: *Jul. 3, 2012

(54) LNG SAMPLING CYLINDER AND METHOD

(75) Inventors: Brian H. Welker, Fulshear, TX (US);
Tracy Dean Peebles, Houston, TX (US);
Dennis M. McKay, Richmond, TX (US)

(73) Assignee: Welker, Inc., Sugar Land, TX (US)

( * ) Notice: Subject to any disclaimer, the term of this patent is extended or adjusted under 35 U.S.C. 154(b) by 791 days.

This patent is subject to a terminal disclaimer.

(21) Appl. No.: 12/234,602

(22) Filed: Sep. 19, 2008

(65) Prior Publication Data

US 2010/0071484 A1    Mar. 25, 2010

(51) Int. Cl.
*G01N 1/10*    (2006.01)
*G01N 1/42*    (2006.01)
(52) U.S. Cl. .................... 73/863.11; 73/864.62
(58) Field of Classification Search ............. 73/863.11, 73/864.62; 374/36
See application file for complete search history.

(56) References Cited

U.S. PATENT DOCUMENTS

| | | | | |
|---|---|---|---|---|
| 2,791,698 | A | * | 5/1957 | Dyroff et al. ............... 250/429 |
| 4,457,171 | A | | 7/1984 | Gebauer |
| 4,628,750 | A | | 12/1986 | Welker |
| 4,922,764 | A | | 5/1990 | Welker |
| 5,337,822 | A | * | 8/1994 | Massie et al. ............... 166/264 |
| 5,526,680 | A | * | 6/1996 | McLaughlin ................ 73/54.01 |
| 6,116,098 | A | * | 9/2000 | Lubek et al. ........... 73/863.11 X |
| 6,422,737 | B1 | | 7/2002 | Welker |
| 7,481,125 | B2 | * | 1/2009 | Mayeaux ................... 73/864.62 |
| 2008/0041163 | A1 | * | 2/2008 | Tohidi et al. .................. 73/659 |
| 2011/0192237 | A1 | * | 8/2011 | Bombulie et al. ......... 73/863.11 |

OTHER PUBLICATIONS

Refrigerated Light Hydrocarbon fluids-Sampling of Liquefied Natural Gas—Continuous and Intermittent Methods, International Standard 8943, Second Edition, Mar. 1, 2007, pp. i-vi and 1-20.
Natural Gas—Sampling Guidelines, International Standard 10715, First Edition, Jun. 1, 2007, pp. i-iV and 1-40.
Obtaining Natural Gas Samples for Analysis by Gas Chromatography, Gas Processors Association, GPA Standard 2166-05, Revised 2005, Tulsa, Oklahoma, www.gasprocessors.com, pp. 1-42.
Manual of Petroleum Measurement Standards, Chapter 14—Natural Gas Fluids Measurement, Section 1—Collecting and Handling of Natural Gas Samples for Custody Transfer, Sixth Edition, Feb. 2006, 6 pages then pages.

* cited by examiner

*Primary Examiner* — Thomas P Noland
(74) *Attorney, Agent, or Firm* — Husch Blackwell LLP

(57) ABSTRACT

A sampling cylinder for LNG (liquefied natural gas) is provided. The sampling cylinder includes a piston cylinder arrangement having opposite end members closing the chamber inside the cylinder. Various porting arrangements are provided for allowing fluid to be fed into a chamber inside the cylinder on opposite sides of a piston. A sample chamber is provided at one end member of the cylinder. The end member containing the sample chamber is also provided with a heat exchanger that may be connected to a source of coolant and preferably the LNG to be sampled to effect cooling of the end member at least partially prior to the sample chamber having a sample of LNG injected thereinto.

5 Claims, 3 Drawing Sheets

LNG SAMPLING CYLINDER AND METHOD

BACKGROUND OF INVENTION

The collection of samples of LNG for subsequent analysis is well known. Analysis is typically performed to determine the BTU value of the natural gas as its component compounds can vary and stratify. Historically, LNG and other forms of natural gas were sold by volume disregarding the BTU content of the natural gas. Natural gas is comprised of several component compounds and is not a "pure compound". It may contain methane, ethane, propane, moisture and other components. Each of the components has its own BTU value, if any. As the value of hydrocarbons used to produce heat has increased, it is important to know its BTU value in order to properly price the product both from a seller perspective and a consumer perspective. LNG is transported by tanker ships, limited distances of pipeline and the like. When loading to or offloading LNG from a ship, it can be substantially continuously sampled and analyzed on site during the loading/offloading process to accommodate variation in the makeup of LNG. This process historically involves the vaporization of the LNG prior to a sample being taken or analyzed. A sample can also be taken at this point and sent away for laboratory analysis. The samples are usually taken using a sampling cylinder into which the LNG, which has been vaporized into a gas, is injected, stored and transported to an analytical facility for analysis. However, this precludes the ability to take a sample of the LNG in the liquid state, eliminating any question about what might have been altered in the vaporization process. It is important to obtain representative samples of the LNG. Because of the different components making up LNG, the obtaining of a representative sample can be difficult since the LNG can stratify if stored static, can fractionate by allowing lower boiling point fractions to evaporate or flash off from the sample. Further, if the LNG vaporizes, its volumetric increase from liquid to vapor can be on the order of a 600 fold increase in volume and result in a dramatic increase in pressure.

LNG is typically maintained at a temperature of approximately $-256°$ F. and at a gage pressure of 40 psi to maintain it in liquid form. If this pressure is reduced or the temperature increased, vaporization of one or more components can occur. Vaporization of the various components will occur at different temperatures and pressures because they are different chemical compounds. Sampling cylinders of the piston type are well known in the art, see for example, U.S. Pat. Nos. 4,628,750 and 4,922,764, both assigned to Welker Engineering Company. The entire disclosures of these patents are incorporated herein by reference. See also U.S. Pat. No. 6,422,737 also assigned to Welker Engineering Company. This latter patent discloses the use of an integral mixing pump to maintain a more homogenous sample. The entire disclosure of this patent is also incorporated herein by reference.

While sampling cylinders are known in the art, an improvement therein is desirable to effect a more uniform and representative sample during the injection of the sample into the sampling cylinder. The present invention involves an improved sampling cylinder which allows for directly sampling LNG (liquid state) into the cylinder.

SUMMARY OF INVENTION

The present invention involves the provision of a LNG sample cylinder useful in the gathering, storing and transport of an LNG sample. The cylinder includes a tubular member defining a sidewall of a cylinder chamber and having first and second ends. A piston is movably positioned in the chamber and selectively moves toward and away from the first and second ends. A first end member is mounted to the tubular member and covers a first end of the tubular member. A second end member is provided and is mounted to the tubular member and covers the second end of the tubular member. A sample chamber is provided in the second end member and is in flow communication with the cylinder chamber. At least two sample conduits are in flow communication with the sample chamber. The second end member also has a heat exchanger associated therewith and isolated from the sample chamber to preclude flow therebetweeen. The heat exchanger is operable to cool the second end member and sample chamber and at least two heat exchange fluid flow conduits are in flow communication with the heat exchanger.

The present invention also involves the provision of a method of sampling LNG. This method allows for sampling and trapping a portion of the LNG as LNG, not as a vaporized gas. The trapped portion of the LNG can be maintained at temperature if desired, or it can be allowed to vaporize and expand in the security of the sample cylinder without the potential for any component to escape during the sampling and vaporization process. This method also allows for trapping a known volume of LNG in the liquefied state and comparing component percentages to that known fixed or adjustable volume of liquid. The method includes connecting a sampling chamber to a source of LNG for flow communication between the source and the sampling chamber. The sampling chamber and at least a portion of the structure defining the sampling chamber is cooled to a predetermined temperature with LNG from the source. LNG is injected from the source into the cooled sampling chamber. After the sample is received in the sampling chamber, it is sealed so that the LNG sample is contained therein. The sampling chamber cooling is ceased so that the sampling cylinder can be transported to a site for analysis. The sampling chamber is cooled prior to conveying LNG from the source to the sampling chamber as a sample to be stored. The heat exchanger is separated flow wise from the sampling chamber.

DETAILED DESCRIPTION OF DRAWINGS

Like numbers throughout the Figures designate like or similar parts and/or construction.

DETAILED DESCRIPTION

Figure 1:
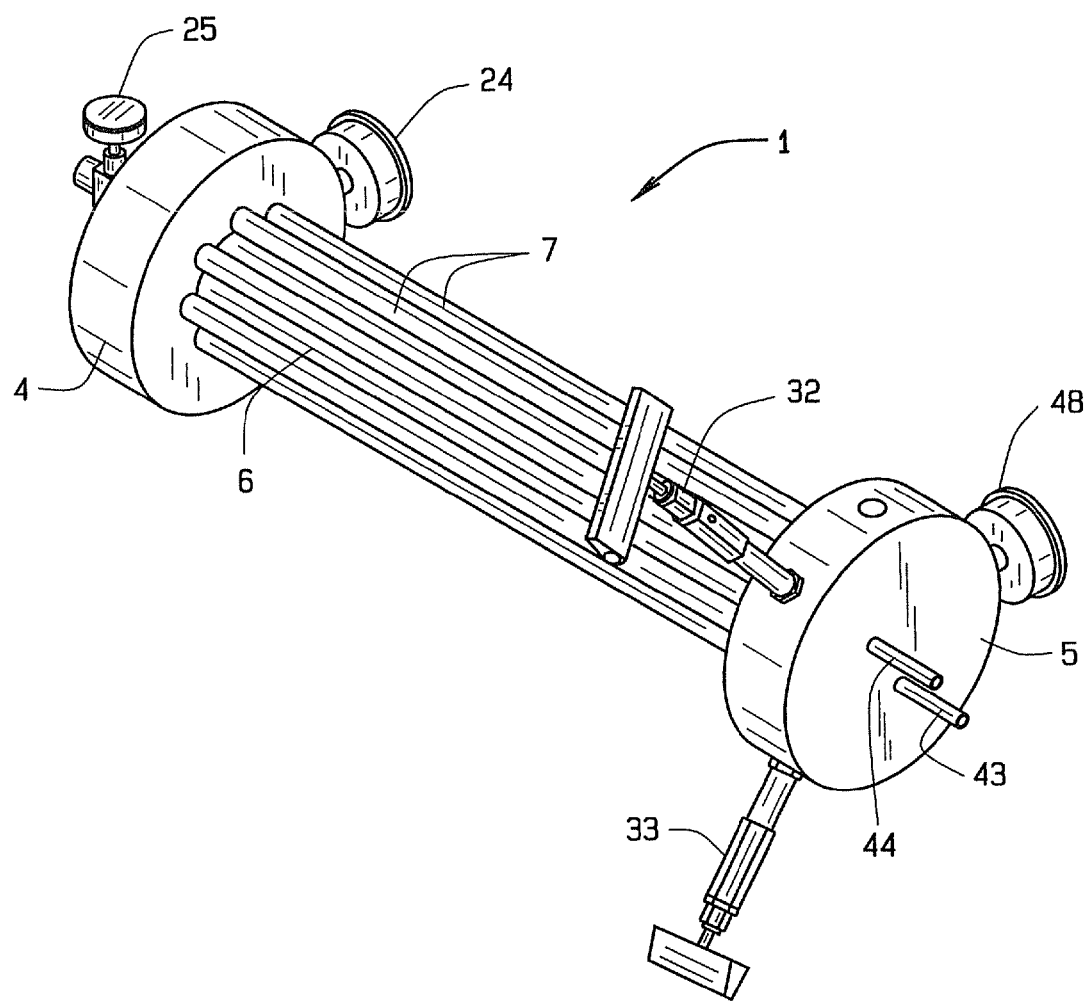
FIG. 1 is an isometric view of a sampling cylinder.
Figure 2:
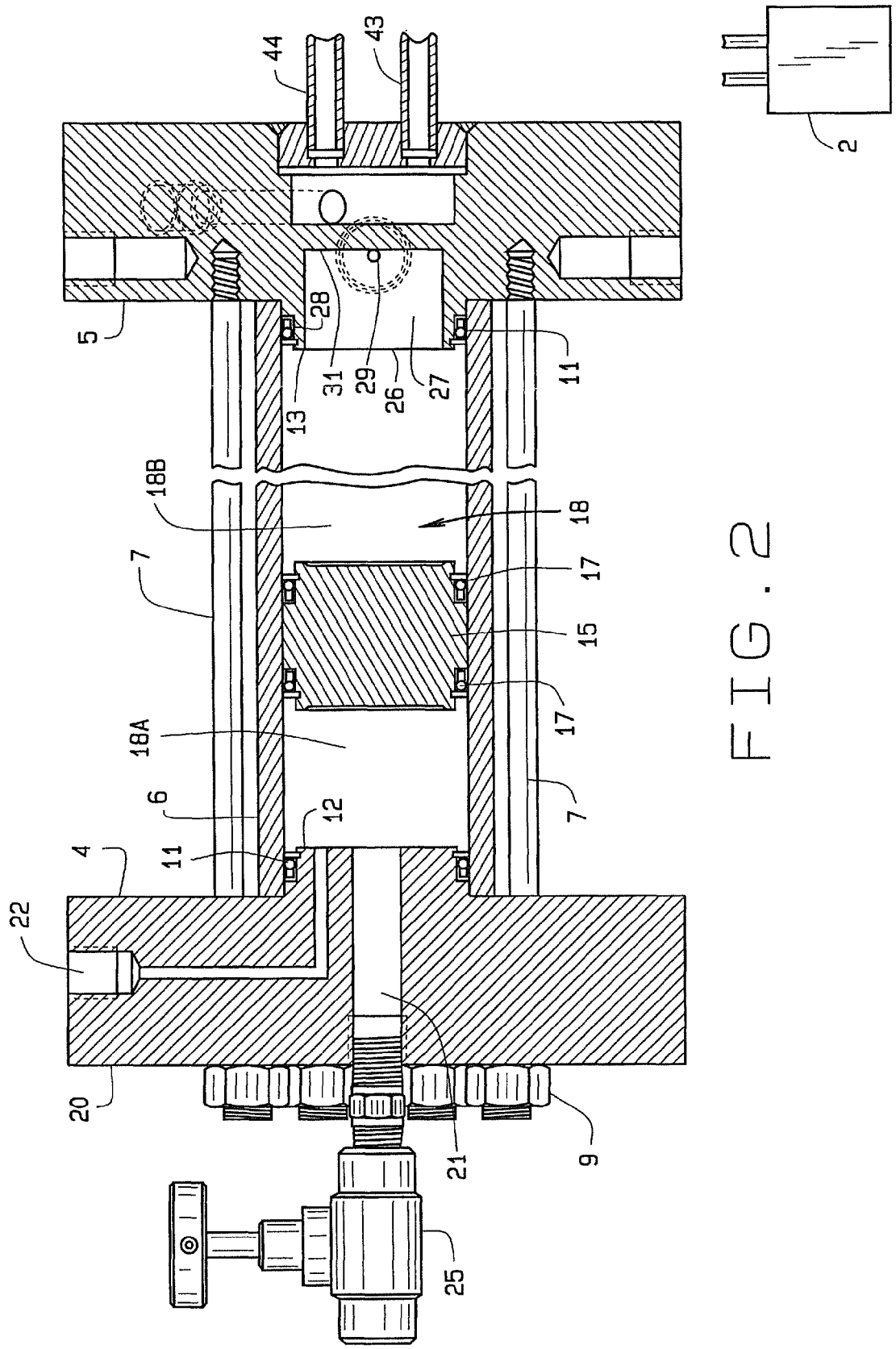
FIG. 2 is a longitudinal cross-sectional view of the sampling cylinder.

The reference numeral 1 designates generally a sampling cylinder that is operable to receive and store LNG (liquefied natural gas) from a source 2 of LNG (FIGS. 1 and 2). The cylinder 1 is selectively connectable to (for flow communication with) and disconnectable from the source 2 as with suitable connecting devices (not shown) to receive and store LNG. The source may be a fixed volume container or a pipeline through which LNG flows. LNG is typically stored at a cold temperature rather than a high elevated pressure to maintain the natural gas in a liquid state. The temperature and pressure at which natural gas liquefies may be easily found from a phase diagram. However, the temperature and pressure may vary by the relative amounts of the various components that make up natural gas as contained in the natural gas. Natural gas is a blend of various components, for example, propane, ethane, methane and other components including moisture (or ice). Typically, LNG has water removed therefrom as is known in the art.

As best seen in FIGS. 1 and 2, the cylinder 1 includes two end closure members 4, 5 each positioned on an opposite end of a cylinder tube 6. Ends 4, 5 may be held in sealing engagement and securement to the tube 6 for example, by tie rods 7 positioned in a circumferential array about the tube 6. The tie rods 6 may be threaded into one end member for example end member 5 and extend through holes in end member 4 and secure the end members 4, 5 in place with threaded fasteners such as hex nuts 9. The end members 4, 5 can be sealed to the interior surface of the tube 6 as with O ring seals 11 mounted on protuberances 12, 13 extending into the interior of the tube 6. Positioned inside tube 6 is a piston 15 that is movable between the end members 4, 5 as determined by the pressure differential on opposite sides of the piston. The piston is mounted for sealing engagement with an interior surface of the tube 6 as with suitable sliding seals 17. The piston 15 divides the chamber 18 formed by the tube 6 and ends 4, 5, into two chambers 18A, 18B. The chamber portion 18A is typically referred to as a precharge chamber and the chamber portion 18B is typically the sample chamber.

The end 4 is provided, in the illustrated structure, with two flow paths 20, 21. The flow path 20 provides communication between a port 22 for the connection of a pressure gage or pressure sensor 24 as seen in FIG. 1. The flow path 20 provides flow communication between the chamber 18A and the port 22 so that the pressure gage 24 can sense pressure of fluid contained within chamber 18A and display the pressure. The flow path 21 provides flow communication between a flow control valve 25 and the chamber 18A. The valve 25 is preferably a manually operated on/off valve that allows for bleeding of fluid from the chamber 18A or the injection of the fluid into the chamber 18A to precharge the chamber 18A with a pressurized fluid such as pressurized nitrogen. Preferably, the fluid in the chamber 18A is a gas. In a preferred embodiment, the usable volume of the chamber 18 is on the order of about 1000 cc's which does not include the volume taken up by the piston 15.

Figure 4:
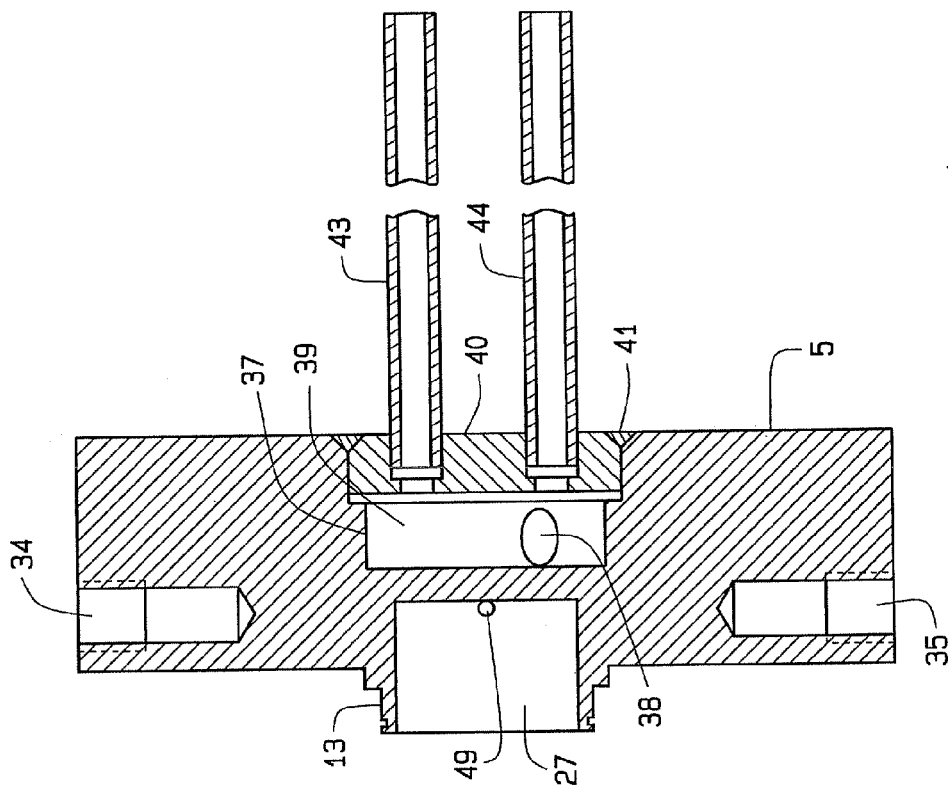
FIG. 4 is an enlarged transverse sectional view of the sampling end member of the sampling cylinder taken along the line 4-4 of FIG. 3.
Figure 3:
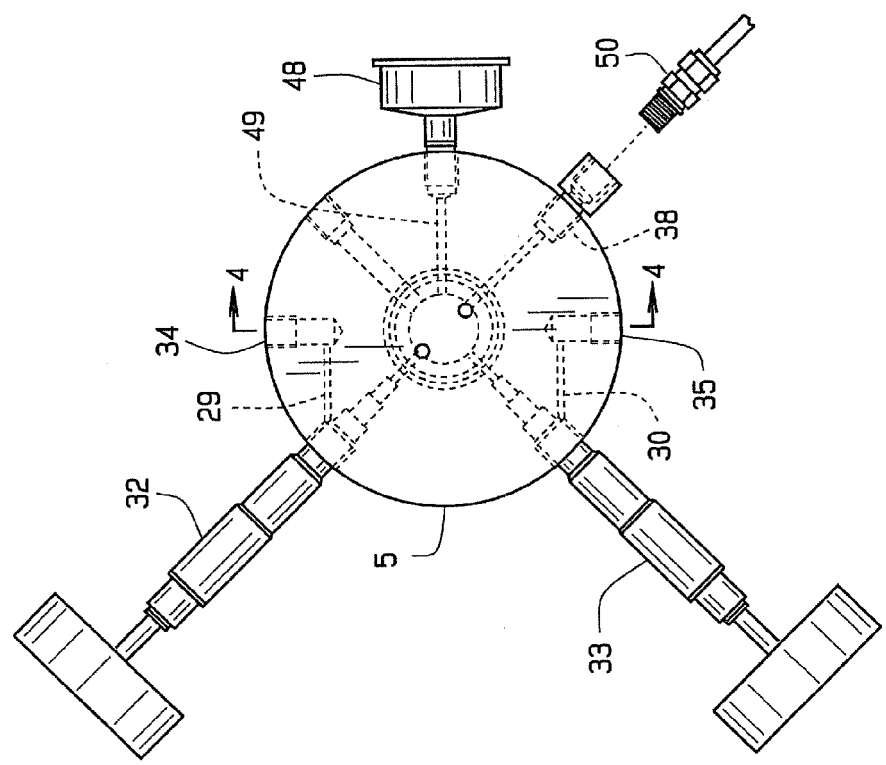
FIG. 3 is an end view of a sampling end of the sampling cylinder with certain flow paths shown in phantom lines.

The end member 5 is adapted for the injection of a sample fluid into and the discharge of a sample fluid from the chamber 18B and a sample chamber 27. The sample chamber 27 has a fixed volume whereas the chamber 18B has a variable volume which volume depends upon the position of the piston 15 within the chamber 18. The sample chamber 27 includes a sidewall 28 and bottom wall 31. The sample chamber 27 has an open side 26 opening into the chamber 18B. The piston 15 overlies the open side 26 when bottomed out. The position of the piston 15 in the chamber 18 will be determined by the relative pressure of the fluids on opposite sides of the piston 15 during operation of the cylinder 1. The details of the construction of the end member 5 are best seen in FIGS. 2, 3 and 4. Two flow paths 29, 30 are provided in the end member 5 to provide flow communication to and from the chamber 27. Shutoff valves 32, 33 are provided to selectively permit flow through the flow paths 29, 30 as described below in more detail in the description of the operation of the present invention. The valves 32, 33 are also operable to completely seal the sample chamber 27 from inflow and outflow once an appropriate sample is captured. Ports 34, 35 are provided for connecting the sample chamber 27 in flow communication with the source 2 through appropriate conduits and for venting the sample chamber 27 during a purge step in the sample taking. In a preferred embodiment, the sample chamber 27 has a volume in the range of between about 10 cc and about 50 cc.

The end member 5 is provided with a fluid flow type heat exchanger adapted for receipt of a heat exchange medium which is preferably derived from the source 2 in the form of cold liquid LNG. Preferably, the heat exchanger 37 is isolated from the sample chamber 27 to prevent flow of fluids therebetween. By having the heat exchanger 37 in the end 5, the entire sampling cylinder 1 need not be cooled in order to obtain a representative sample and prevents or reduces the chance of vaporization of a sample or a portion of the sample during the collection process. An access port 38 is provided for the placing of a temperature probe 50 in temperature sensing or measuring relationship to the end member 5 and heat exchanger 37. As seen, the heat exchanger 37 is a single cavity provided in the end member 5 wherein cold heat exchange fluid will contact the surfaces and cool the end member 5 and hence the chamber 27. As shown, the chamber 39 portion of the heat exchanger 37 is formed as a pocket in the end member 5 by a suitable machining or casting technique having its open end covered by a plug 40 that can be welded as at 41 in place on member 5 to provide a fluid tight seal. The plug 40 is preferably provided with an inlet 43 and an outlet 44 that provide for simultaneous flow communication into and out of the chamber 39. The inlet 43 and outlet 44 may be provided with suitable connectors for connecting them to the source 2 of LNG and to a discharge collection system as is known in the art (not shown) that preferably provides a back pressure on the chamber 39 to keep the LNG liquid. A pressure gage 48 may also be provided by being connected to a port 49 that is flow communication with the chamber 27 to measure or sense the pressure of the fluid within the chamber 27. The temperature probe 50 by monitoring the temperature of the end 5 can provide an indication of the temperature of the fluid both in the heat exchanger 39 and that contained in the chamber 27.

The sampling cylinder 1 can be provided with means to indicate the position of the piston 15 therein. This can be done as disclosed in above-referenced U.S. Pat. Nos. 4,628,750 or 4,922,764 which are incorporated herein by reference. Position of the piston 15 can also be indicated by the use of a sealed rod that will project from the end 5 or any other suitable means.

The present invention is better understood by a description of the operation thereof. When it is desired to sample LNG, a sampling cylinder 1 is provided. A precharge pressurized fluid is provided in the chamber 18A. The pressure is on the order of about 1,000 psi for a typical LNG sampling. By pressurizing the chamber 18A, the piston 15 moves to a bottomed out position in the chamber 18B resting against the protuberance 13. The charging (pressurizing) of the chamber 18A and moving of the piston 15 is done with the chamber 27 in flow communication with the exterior of the cylinder 1 leaving the chamber 27 basically at atmospheric pressure. The chamber 18A is then closed to maintain the pressure. The heat exchanger 37 is then connected via the inlet 43 to a source of liquefied LNG such as the source 2. The LNG will flow into the heat exchange chamber 39 and can be discharged through the outlet 44 to a suitable collection system or can be repressurized and injected back into the source 2. Preferably, after cooling of the end 5 has been completed to the desired temperature for example, less than about −150° F. and preferably the temperature or the approximate temperature of the extracted LNG, for example, less than approximately −256° F., the flow of liquefied LNG can be ceased or can be continued during the charging of the sample to the chamber 27. The inlet port 34 and its flow path 29 are also connected to the source 2 of LNG preferably with the valve 32 closed. The outlet port 35 and its flow path 30 are then connected to the collection system as was the outlet 44. After the flow connections of the ports 34 and 35 are effected, the valve 32 may be opened along with the valve 33 to allow, because of the pressure differential across the ports 34, 35 for LNG to flow into and out of the chamber 27. After a suitable amount of purging time, the valve 33 may be closed to stop outflow, allow the chamber 27 to fill to a predetermined pressure and then the valve 32 may be closed to seal the chamber 27. The piston 15 will move toward the end 4 once the chamber 27 is pressurized. It is to be understand that while a purging process has been disclosed, it is to be understood that the chamber 27 could be filled with a known gas for example nitrogen which can be accommodated for in the analysis. After the sample LNG has been captured, the cylinder 1 may be transported to an analytical 716919.98 facility where the sample LNG is extracted by being discharged either through the port 34 or 35 to analytical equipment such as a gas chromatograph or calorimeter for analysis. Once connected, the appropriate valve 32 or 33 may be opened to permit discharge of the LNG sample. In the event the temperature of the LNG sample rises in the chamber 27, for example during transit, it may vaporize increasing the pressure in the chamber 18A. This would then move the piston 15 further toward the end 4. It is preferred to transport the cylinder 1 with the temperature of the sample below about −150° F., preferably below about −200° F. and most preferably below about −256° F. with the sample being maintained as a liquid.

Thus, there has been shown and described several embodiments of a novel invention. As is evident from the foregoing description, certain aspects of the present invention are not limited by the particular details of the examples illustrated herein, and it is therefore contemplated that other modifications and applications, or equivalents thereof, will occur to those skilled in the art. The terms "having" and "including" and similar terms as used in the foregoing specification are used in the sense of "optional" or "may include" and not as "required". Many changes, modifications, variations and other uses and applications of the present invention will, however, become apparent to those skilled in the art after considering the specification and the accompanying drawings. All such changes, modifications, variations and other uses and applications which do not depart from the spirit and scope of the invention are deemed to be covered by the invention which is limited only by the claims which follow.

What is claimed is:

1. A sample cylinder including:
   a tubular member defining a sidewall of a cylinder chamber and having first and second ends;
   a solid piston movably positioned in the chamber and selectively movable toward and away from the first and second ends, said solid piston having opposing flat end surfaces and sliding seals about the circumference to seal against the sidewall of the tubular member;
   a first end member mounted to the tubular member and covering said first end;
   a second end member mounted to the tubular member and covering said second end;
   a plurality of tie rods connecting said first end member to said second end member to mechanically capture said tubular member;
   a liquefied natural gas sample chamber formed in said second end member and defined by a sidewall, a bottom wall and said solid piston;
   said second end member further defining an inlet to the liquefied natural gas sample chamber and an outlet to the liquefied natural gas sample chamber, both said inlet and said outlet to the liquefied natural gas sample chamber each being secured by a of shut off valve to isolate the liquefied natural gas chamber from atmosphere;
   said second end member further defining a cooling heat exchanger and a cooling heat exchange chamber;
   said cooling heat exchange chamber having an inlet and an outlet in fluid communication with a source of liquefied natural gas to cool the cooling heat exchanger, the second end cap, the sidewall and the bottom wall of the liquefied natural gas chamber; and
   said second end member, said cooling heat exchanger, said inlet and said outlet to said cooling heat exchanger, said solid piston, said tubular member, the first and the second sliding seals and a O-ring seal to seal said second end member to said tubular member are all capable of withstanding temperatures down to about −256° F.

2. The apparatus of claim 1 wherein the first end member, the sidewall of the tubular member and the solid piston define a precharge chamber capable of withstanding pressures of at least about 1,000 psi.

3. The apparatus of claim 2 further including a first shut off valve mounted in the first end member, said first shut off valve in fluid communication with said precharge chamber to isolate said precharge chamber from atmosphere and a pressure sensor mounted in the first end member in fluid communication with the precharge chamber to sense the pressure in the precharge chamber.

4. The apparatus of claim 3 further including a second shut off valve mounted in the second end member to control flow through an inlet port to said liquefied natural gas sample chamber and a third shut off valve mounted in the second end member to control flow through an outlet port from said liquefied natural sample chamber.

5. The apparatus of claim 4 wherein said liquefied natural gas sample chamber has a volume in the range of between about 10 cc and about 50 cc.

* * * * *